US008748683B2

(12) United States Patent
Butler

(10) Patent No.: US 8,748,683 B2
(45) Date of Patent: Jun. 10, 2014

(54) DILUTE LIQUID PHASE ALKYLATION

(71) Applicant: Fina Technology, Inc., Houston, TX (US)

(72) Inventor: James R. Butler, Spicewood, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 13/785,851

(22) Filed: Mar. 5, 2013

(65) Prior Publication Data

US 2013/0184508 A1 Jul. 18, 2013

Related U.S. Application Data

(63) Continuation of application No. 13/024,602, filed on Feb. 10, 2011, now Pat. No. 8,426,661, and a continuation of application No. 11/650,282, filed on Jan. 5, 2007, now abandoned.

(60) Provisional application No. 60/756,778, filed on Jan. 7, 2006.

(51) Int. Cl.
C07C 2/66 (2006.01)

(52) U.S. Cl.
USPC .......................................................... 585/467

(58) Field of Classification Search
USPC .......................................................... 585/467
See application file for complete search history.

(56) References Cited

U.S. PATENT DOCUMENTS

| | | | | |
|---|---|---|---|---|
| 4,891,458 A | * | 1/1990 | Innes et al. | 585/323 |
| 5,082,990 A | * | 1/1992 | Hsieh et al. | 585/467 |
| 5,430,211 A | * | 7/1995 | Pogue et al. | 585/323 |

* cited by examiner

Primary Examiner — Thuan D Dang

(57) ABSTRACT

Methods of forming ethylbenzene are described herein. In one embodiment, the method includes contacting dilute ethylene with benzene in the presence of an alkylation catalyst to form ethylbenzene, wherein such contact occurs in a liquid phase reaction zone and recovering ethylbenzene from the reaction zone.

24 Claims, 1 Drawing Sheet

DILUTE LIQUID PHASE ALKYLATION

CROSS-REFERENCE TO RELATED APPLICATIONS

This application is a continuation of U.S. Application Ser. No. 13/024,602, filed on Feb. 10, 2011, which is a continuation of U.S. application Ser. No. 11/650,282, filed on Jan. 5, 2007, now abandoned, which claims the benefit of U.S. Provisional Application No. 60/756,778, filed on Jan. 7, 2006.

FIELD

Embodiments of the present invention generally relate to liquid phase alkylation. In particular, embodiments of the present invention relate to dilute ethylation of benzene in the liquid phase.

BACKGROUND

As a result of the high cost of pure (or high purity) ethylene, efforts have been directed to utilizing dilute ethylene in the alkylation of benzene to form ethylbenzene.

While it has been discovered that the use of dilute ethylene generally results in low xylene formation, the high methane and hydrogen content thereof generally results in a bubble point temperature of the combined mixture of dilute ethylene and benzene that is very low. For example, the bubble point temperature may be lower than the activity temperature of the ethylation catalyst. Accordingly, it has not been possible for liquid phase alkylation of dilute ethylene.

Therefore, a need exists to develop a method of utilizing lower cost ethylene in liquid phase alkylation.

SUMMARY

Embodiments of the invention generally include methods of forming ethylbenzene. In one embodiment, the method includes contacting dilute ethylene with benzene in the presence of an alkylation catalyst to form ethylbenzene, wherein such contact occurs in a liquid phase reaction zone and recovering ethylbenzene from the reaction zone.

In another embodiment, the method includes contacting dilute ethylene with benzene in the presence of cerium promoted zeolite alkylation catalyst to form ethylbenzene.

In yet another embodiment, the method includes introducing benzene to a liquid phase reaction zone having an alkylation catalyst disposed therein, introducing dilute ethylene to the liquid phase reaction zone, wherein the dilute ethylene is introduced in a manner to contact the benzene and the alkylation catalyst and recovering a product stream from the reaction zone, wherein the product stream comprises 0.8 wt. % or less butylbenzene.

In yet another embodiment, the method includes contacting benzene with dilute ethylene in a benzene:ethylene ratio of about 8:1 or less, wherein the contact occurs in the presence of an alkylation catalyst disposed within a liquid phase reaction zone and recovering ethylbenzene from the liquid phase reaction zone.

DETAILED DESCRIPTION

Introduction and Definitions

Figure 1A:
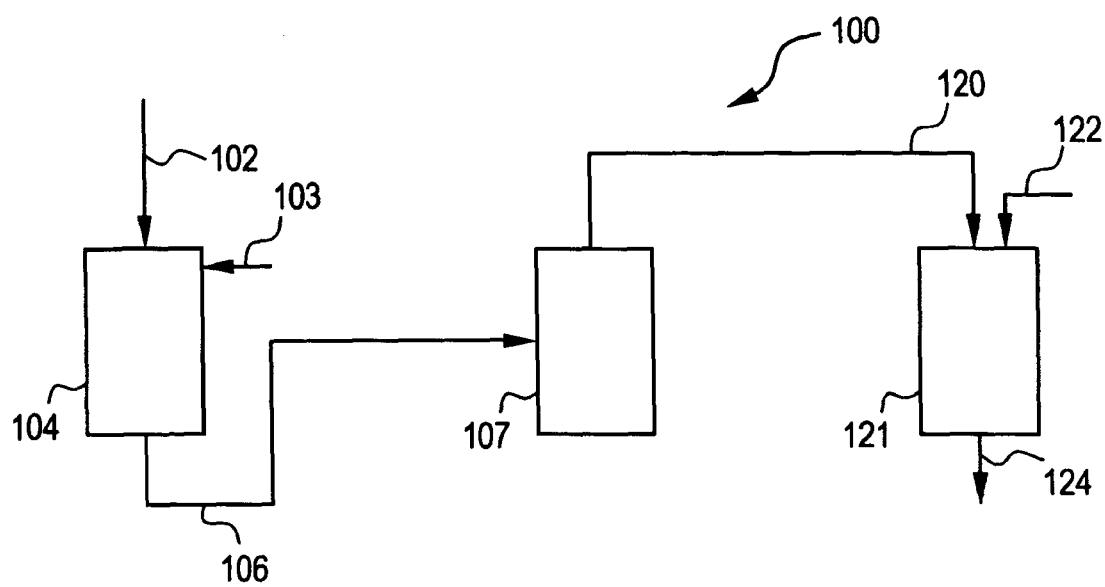
FIGS. 1A and 1B illustrate an embodiment of an alkylation/transalkylation process.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

The term "activity" refers to the weight of product produced per weight of the catalyst used in a process per hour of reaction at a standard set of conditions (e.g., grams product/gram catalyst/hr).

The term "alkyl" refers to an alkane absent hydrogen.

The term "alkylation" refers to the transfer of an alkyl group from one molecule to another.

The term "deactivated catalyst" refers to a catalyst that has lost enough catalyst activity to no longer be efficient in a specified process. Such efficiency is determined by individual process parameters.

The term "olefin" refers to a hydrocarbon with a carbon-carbon double bond.

The term "processing" is not limiting and includes agitating, mixing, milling, blending and combinations thereof, all of which are used interchangeably herein. Unless otherwise specified, the processing may occur in one or more vessels, such vessels being known to one skilled in the art.

The term "recycle" refers to returning an output of a system as input to either that same system or another system within a process. The output may be recycled to the system in any manner known to one skilled in the art, for example, by combining the output with an input stream or by directly feeding the output into the system. In addition, multiple input/recycle streams may be fed to a system in any manner known to one skilled in the art.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

FIG. 1A illustrates a schematic block diagram of an embodiment of an alkylation/transalkylation process 100. Although not shown herein, the process stream flow may be modified based on unit optimization so long as the modification complies with the spirit of the invention, as defined by the claims. For example, at least a portion of any overhead fraction may be recycled as input to any other system within the process and/or any process stream may be split into multiple process stream inputs, for example. Also, additional process equipment, such as heat exchangers, may be employed throughout the processes described herein and such placement is generally known to one skilled in the art. Further, while described below in terms of primary components, the streams indicated below may include any additional components as known to one skilled in the art.

The process 100 generally includes supplying an input stream 102 to an alkylation system 104. The alkylation system 104 is generally adapted to contact the input stream 102 with an alkylation catalyst to form an alkylation output stream 106. In addition to the input stream 102, an additional input, such as an alkylating agent, is generally supplied to the alkylation system 104 via line 103.

At least a portion of the alkylation output stream 106 passes to a separation system 107. The separation system 107 generally includes a plurality of vessels, such vessels being adapted to separate components of the output stream 106. At least a portion of the separation system output, described in further detail below, is passed from the separation system 107 to a second alkylation system (i.e., a transalkylation system 121) as transalkylation input 120.

In addition to the transalkylation input 120, an additional input, such as additional aromatic compound, is generally supplied to the transalkylation system 121 via line 122 to contact a transalkyation catalyst and form a transalkylation output 124.

The input stream 102 generally includes a first aromatic compound. The aromatic compound may include substituted or unsubstituted aromatic compounds. In a specific embodiment, the first aromatic compound includes benzene. The benzene may be supplied from a variety of sources, such as a fresh benzene source and/or a variety of recycle sources. As used herein, the term "fresh benzene source" refers to a source including at least about 95 wt. % benzene, at least about 98 wt. % benzene or at least about 99 wt. % benzene, for example. As used herein, the term "recycle" refers to an output of a system, such as an alkylation system and/or a dehydrogenation system, which is then returned as input to either that same system or another system the same process.

The alkylating agent 103 generally includes ethylene. In a specific embodiment, the alkylating agent includes dilute ethylene. As used herein, the term "dilute ethylene" refers to alkylating agent streams having less than about 50% ethylene. For example, the alkylating agent may include from about 7% to about 25% or from about 10% to about 15% ethylene. The dilute ethylene stream may further include methane, hydrogen or ethane, for example.

Dilute ethylene may be supplied from any source known to one skilled in the art. For example, the dilute ethylene may be produced from fluid catalytic cracking (FCC).

In addition to the first aromatic compound and the alkylating agent, the input stream 102 may further include other compounds in minor amounts (e.g., sometimes referred to as poisons or inactive compounds,) such as toluene, ethyl benzene, $C_7$ aliphatic compounds and/or nonaromatic compounds, for example. In one embodiment, the input stream 102 includes less than about 3% of such compounds or less than about 1%, for example.

The alkylation system 104 generally includes one or more reaction vessels. The reaction vessels may include continuous flow reactors (e.g., fixed-bed, slurry bed or fluidized bed,) for example. In one embodiment, the alkylation system 104 includes a plurality of multi-stage reaction vessels (not shown). For example, the plurality of multi-stage reaction vessels may include a plurality of operably connected catalyst beds, such beds containing an alkylation catalyst (not shown.) The number of catalyst beds is generally determined by individual process parameters, but may include from 2 to 20 catalyst beds or from 3 to 10 catalyst beds, for example.

Such reaction vessels are generally liquid phase reactors operated at reactor temperatures and pressures sufficient to maintain the alkylation reaction in the corresponding phase, i.e., the phase of the aromatic compound, for example. In one embodiment, the plurality of stages within a reaction vessel may be operated with the same or different catalyst and at the same or different temperatures and space velocities. Such temperatures and pressures are generally determined by individual process parameters. However, liquid phase reactions may occur at temperatures of from about 160° C. to about 270° C. at 600 psig.

The alkylation catalyst generally includes a cerium promoted molecular sieve catalyst. In one embodiment, the cerium promoted catalyst is a cerium promoted zeolite beta catalyst. The cerium promoted zeolite (e.g., cerium beta) catalyst may be formed from any zeolite catalyst known to one skilled in the art. For example, the cerium beta catalyst may include zeolite beta modified by the inclusion of cerium. Any method of modifying the zeolite beta catalyst with cerium may be used.

The zeolite beta may have a silica to alumina molar ratio (expressed as $SiO_2/Al_2O_3$) of from about 10 to about 200 or about 20 to about 150, for example. In one embodiment, the zeolite beta may have a low sodium content, e.g., less than about 0.2 wt. % expressed as $Na_2O$, or less than about 0.02 wt. %, for example. The sodium content may be reduced by any method known to one skilled in the art, such as through ion exchange, for example. The formation of zeolite beta is further described in U.S. Pat. Nos. 3,308,069 and 4,642,226, which are incorporated by reference herein.

In another embodiment, it is contemplated that a cerium promoted zeolite Y catalyst may be used. It is further contemplated that the zeolite Y catalyst may be modified with cerium in the same manner as the modification of zeolite beta. The formation of Zeolite Y is described in U.S. Pat. No. 4,185,040, which is incorporated by reference herein.

The alkylation catalyst may optionally be bound to, supported on or extruded with any support material. For example, the alkylation catalyst may be bound to a support to increase the catalyst strength and attrition resistance. The support material may include alumina, silica, aluminosilicate, titanium and/or clay, for example.

The alkylation output 106 generally includes a second aromatic compound formed from the reaction of the first aromatic compound and the alkylating agent in the presence of the alkylation catalyst, for example. In a specific embodiment, the alkylation output 106 includes ethylbenzene. The alkylation output 106 further includes less than about 1 wt. %, or less than about 0.8 wt. % or less than about 0.2 wt. % butylbenzenes, such as sec-butylbenzene, for example.

The transalkylation system 120 generally includes one or more reaction vessels having a transalkylation catalyst disposed therein. The reaction vessels may include any reaction vessel, combination of reaction vessels and/or number of reaction vessels (either in parallel or in series) known to one skilled in the art. Such temperatures and pressures are generally determined by individual process parameters. However, liquid phase reactions may occur at temperatures of from about 65° C. to about 290° C. (e.g., the critical temperature of the first aromatic compound) and pressures of from about 600 psig or less, for example. Vapor phase reactions may occur at temperatures of from about 420° C. to about 450° C., for example.

The transalkylation output 124 generally includes the second aromatic compound, for example. As stated previously, any of the process streams, such as the transalkylation output 124, may be used for any suitable purpose or recycled back as input to another portion of the system 100, such as the separation system 107, for example.

The transalkylation catalyst may include a molecular sieve catalyst and may be the same catalyst or a different catalyst than the alkylation catalyst, for example. Such molecular sieve catalyst may include zeolite beta, zeolite Y, zeolite MCM-22, zeolite MCM-36, zeolite MCM-49 or zeolite MCM-56, for example.

In a specific embodiment, the first aromatic compound includes benzene and the alkylating agent includes dilute ethylene. In one embodiment, the molar ratio of benzene to ethylene in the input stream 102 may be about 10:1 or less, or about 8:1 or less or about 6:1 or less in each catalyst bed and the space velocity may be from about 2 to about 100, for example.

In a specific embodiment, benzene is recovered through line 110 and recycled (not shown) as input to the alkylation system 104, while ethylbenzene and/or polyalkylated benzenes are recovered via lines 116 and 120 respectively.

Figure 1B:
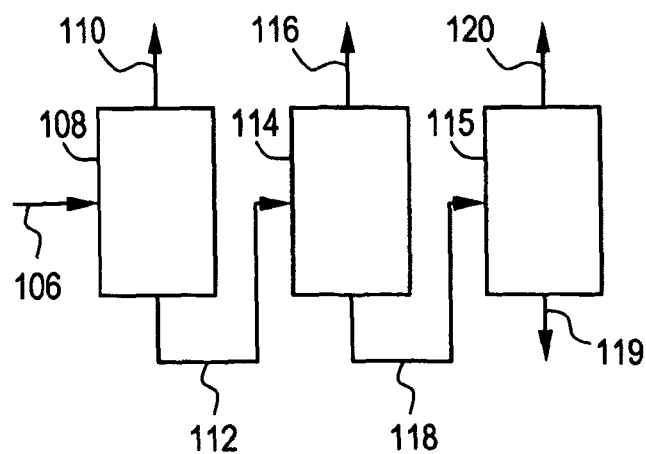

In a specific embodiment, the separation system (or product recovery) 107 includes three separation zones (illustrated in FIG. 1B) operated at conditions known to one skilled in the art. The first separation zone 108 may include any process or combination of processes known to one skilled in the art for the separation of aromatic compounds. For example, the first separation zone 108 may include one or more distillation columns (not shown,) either in series or in parallel. The number of such columns may depend on the volume of the alkylation output 106 passing therethrough, for example. While the temperature and pressure are system specific, the first separation zone temperature may be from about 130° C. to about 170° C. and the pressure may be atmospheric pressure to 50 psig, for example.

The overhead fraction 110 from the first column 108 generally includes the first aromatic compound, such as benzene, for example.

The bottoms fraction 112 from the first separation zone 108 generally includes the second aromatic compound, such as ethylbenzene, for example. The bottoms fraction 112 further includes additional components, which may undergo further separation in the second separation zone 114 and third separation zone 115, discussed further below.

The second separation zone 114 may include any process known to one skilled in the art, for example, one or more distillation columns (not shown), either in series or in parallel. While the temperature and pressure are system specific, the first separation zone temperature may be from about 180° C. to about 240° C. and the pressure may be from about 100 psig to about 500 psig, for example.

The overhead fraction 116 from the second separation zone 114 generally includes the second aromatic compound, such as ethylbenzene, which may be recovered and used for any suitable purpose, such as the production of styrene, for example.

The bottoms fraction 118 from the second separation zone 114 generally includes heavier aromatic compounds, such as polyethylbenzene, cumene and/or butylbenzene, for example, which may undergo further separation in the third separation zone 115.

The third separation zone 115 generally includes any process known to one skilled in the art, for example, one or more distillation columns (not shown), either in series or in parallel. While the temperature and pressure are system specific, the first separation zone temperature may be from about 180° C. to about 240° C. and the pressure may be atmospheric pressure to about 50 psig, for example.

In a specific embodiment, the overhead fraction 120 from the third separation zone 115 may include diethylbenzene and liquid phase triethylbenzene, for example. The bottoms fraction 119 (e.g., heavies) may be recovered from the third separation zone 115 for further processing and recovery (not shown).

Unfortunately, alkylation and transalkylation catalysts generally experience deactivation upon exposure to reaction. The life of the catalyst generally depends on process conditions and catalyst type. However, when regeneration of any catalyst within the system is desired, the regeneration procedure generally includes processing the deactivated catalyst at high temperatures, although the regeneration may include any regeneration procedure known to one skilled in the art.

Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the catalyst to a temperature or a series of temperatures, such as a regeneration temperature of from about 50° C. to about 200° C. above the purging or reaction temperature, for example.

In one embodiment, the catalyst is heated to a first temperature (e.g., 700° F.) for a time sufficient to provide an output stream having an oxygen content of about 0.5%. The catalyst may then be heated to a second temperature for a time sufficient to provide an output stream having an oxygen content of about 2.0%. The second temperature may be about 50° F. greater than the first temperature, for example. The second temperature is generally about 950° F. or less, for example. The catalyst may further be held at the second temperature for a period of time, or at a third temperature that is greater than the second temperature, for example.

Upon catalyst regeneration, the catalyst may then be reused for alkylation and transalkylation, for example.

Unexpectedly, no increase in the butylbenzene yield was observed.

While the foregoing is directed to embodiments of the present invention, other and further embodiments of the invention may be devised without departing from the basic scope thereof and the scope thereof is determined by the claims that follow.

What is claimed is:

1. A method of forming ethylbenzene comprising:
contacting a dilute ethylene stream with benzene at a molar ratio of benzene to ethylene of about 10:1 or less in a catalyst bed in a presence of an alkylation catalyst comprising a zeolite beta promoted with cerium and having a silica to alumina molar ratio of from about 10:1 to about 200:1 to thereby react the benzene with the ethylene, forming ethylbenzene and the catalyst becomes deactivated, wherein the contact occurs in a liquid phase reaction zone, and wherein the dilute ethylene stream comprises less than about 50% ethylene, and wherein the dilute ethylene stream is produced from fluid catalytic cracking;

recovering a product stream comprising the ethylbenzene from the liquid phase reaction zone; and regenerating the deactivated alkylation catalyst to produce a regenerated catalyst comprising:

taking a reactor of the liquid phase reaction zone offline;

purging the alkylation catalyst disposed in the reactor with an inert gas at a purging temperature;

heating the alkylation catalyst to a first temperature for a time period sufficient to provide an output stream having an oxygen content of about 0.5%;

heating the alkylation catalyst to a second temperature higher than the first temperature for time period sufficient to provide an output stream having an oxygen content of about 2.0%; wherein the first and second temperature are from about 50° C. to 200° C. above the purging temperature; and reusing the regenerated catalyst.

2. The method of claim 1, wherein the benzene and the dilute ethylene stream are separately introduced into the liquid phase reaction zone.

3. The method of claim 1, wherein the benzene to ethylene ratio is about 8:1 or less in the catalyst bed.

4. The method of claim 1, wherein the benzene:ethylene ratio is about 6:1 or less in the catalyst bed.

5. The method of claim 1, wherein the dilute ethylene stream comprises from about 7% to about 25% ethylene.

6. The method of claim 1, wherein the dilute ethylene stream comprises from about 10% to about 15% of the ethylene.

7. The method of claim 1, wherein the product stream comprises 1 wt. % or less butylbenzene.

8. The method of claim 1, wherein the product stream comprises 0.8 wt. % or less butylbenzene.

9. The method of claim 1, wherein the product stream comprises 0.2 wt. % or less butylbenzene.

10. The method of claim 1, wherein a remainder of the dilute ethylene stream comprises methane, hydrogen, or ethane.

11. The method of claim 1, wherein the dilute ethylene stream comprises methane and hydrogen.

12. The method of claim 11, wherein the dilute ethylene stream further comprises ethane.

13. The method of claim 1, wherein the alkylation catalyst comprises less than about 0.2 wt % $Na_2O$.

14. The method of claim 1, wherein reaction in the liquid phase reaction zone occurs at a temperature of from 160° C. to 270° C. at 600 psig.

15. The method of claim 1, wherein an input stream comprising the benzene is introduced into the liquid phase reaction zone, and wherein the input stream is a fresh benzene source.

16. The method of claim 1, wherein an input stream comprising the benzene is introduced into the liquid phase reaction zone, and wherein the input stream comprises at least about 95 wt. % benzene.

17. The method of claim 1, wherein the liquid phase reaction zone is in a continuous flow reactor.

18. The method of claim 17, wherein the continuous flow reactor is a fixed-bed reactor, a slurry bed reactor, or fluidized bed reactor.

19. The method of claim 1, wherein the benzene is present in a molar excess to the ethylene.

20. The method of claim 1, wherein the molar ratio of benzene to ethylene is from about 6:1 to about 10:1.

21. The method of claim 1, wherein the liquid phase reaction zone is maintained at temperatures and pressures sufficient to maintain the alkylation reaction in the liquid phase.

22. The method of claim 1, wherein an input stream comprising the benzene is introduced into the liquid phase reaction zone, and wherein the input stream further comprises poisons.

23. The method of claim 1, further comprising regenerating the alkylation catalyst; and reusing the regenerated alkylation catalyst in place of the alkylation catalyst in the process of claim 1;

wherein use of the regenerated alkylation catalyst does not exhibit an increase in the amount of butylbenzene yield in comparison to the amount of butylbenzene yield exhibited by use of the alkylation catalyst.

24. The method of claim 23, wherein the product stream comprises 1 wt. % or less butylbenzene when produced using the regenerated alkylation catalyst.

* * * * *